United States Patent [19]

Nagpal et al.

[11] Patent Number: 6,034,110
[45] Date of Patent: Mar. 7, 2000

[54] METHOD FOR PREVENTING ONSET OF RESTENOSIS AFTER ANGIOPLASTY EMPLOYING AN RXR-SPECIFIC RETINOID AND A PPARγ LIGAND

[75] Inventors: Sunil Nagpal, Lake Forest; Roshantha A. Chandraratna, Mission Viejo, both of Calif.

[73] Assignee: Allergan Sales, Inc., Irvine, Calif.

[21] Appl. No.: 09/005,790

[22] Filed: Jan. 12, 1998

[51] Int. Cl.[7] .................. A61K 31/44; A61K 31/425; A61K 31/415; A61K 31/38; A61K 31/19
[52] U.S. Cl. .................. 514/350; 514/345; 514/365; 514/398; 514/400; 514/448; 514/461; 514/568; 514/569
[58] Field of Search .................. 514/350, 345, 514/568, 448, 461, 398, 400, 365, 569

[56] References Cited

U.S. PATENT DOCUMENTS

| | | | |
|---|---|---|---|
| 5,116,864 | 5/1992 | March et al. | 514/455 |
| 5,140,012 | 8/1992 | McGovern et al. | 514/19 |
| 5,166,143 | 11/1992 | Ondetti et al. | 514/89 |
| 5,213,561 | 5/1993 | Weinstein et al. | 600/7 |
| 5,455,265 | 10/1995 | Chandraratna | 514/448 |

FOREIGN PATENT DOCUMENTS

96/33724  10/1996  WIPO .

OTHER PUBLICATIONS

Serruys et al, "Incidence of restenosis after successful coronary angioplasty: a time–related phenomenon. A quantitative angiographic study in 342 consecutive patients at 1,2,3, and 4 months" Therapy and Prevention–Coronary Angioplasty; vol. 77, No. 2, Feb. 1988; pp. 361–371.

Schoojans et al, "The peroxisome proliferator activated receptors (PPARs) and their effects on lipid metabolism and adipocyte differentiation"; Biochimica Biophysica Acta; 1302 (1996); pp. 93–109.

Dubey et al, "Pioglitazone attenuates hypertension and inhibits growth of renal arteriolar smooth muscle in rats", Am. J. Physiol., Oct. 1993; pp. R726–32.

*Primary Examiner*—Theodore J. Criares
*Attorney, Agent, or Firm*—Carlos A. Fisher; Robert J. Baran; Martin A. Voet

[57] ABSTRACT

A method is provided for preventing or reducing the risk of restenosis following angioplasty by administering a retinoid, such as an RXR-selective retinoid, e.g. the compound of the formula:

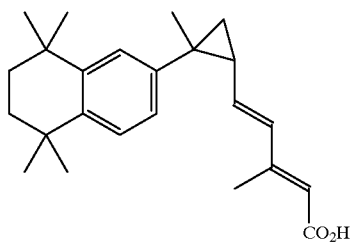

and a PPARγ specific ligand and pharmaceutically acceptable salts and esters and amides thereof.

20 Claims, 5 Drawing Sheets

METHOD FOR PREVENTING ONSET OF RESTENOSIS AFTER ANGIOPLASTY EMPLOYING AN RXR-SPECIFIC RETINOID AND A PPARγ LIGAND

FIELD OF THE INVENTION

The present invention relates to a method for preventing onset or recurrence of restenosis after angioplasty procedures by administering an RXR-specific agonist retinoid alone or in combination with a PPARγ ligand, thereby inhibiting proliferation of vascular smooth muscle cells.

BACKGROUND OF THE INVENTION

Approximately 30–40% of atherosclerotic coronary arteries treated by angioplasty or by bypass surgery occlude as a result of restenosis. Vascular smooth muscle cell (VSMC) proliferation and migration are critical events in the development of restenosis and in the progression of atherosclerosis.

Percutaneous transluminal angioplasty (PTA), defined as any percutaneous transluminal method of decreasing stenosis within a blood vessel, whether caused by the existence of an atheromatous plaque, thrombosis, embolus, and/or mineral deposit, by any of a number of means such as balloon dilation, thermal ablation, laser atherectomy, mechanical shaving, extraction or ultrasonic pulverization, hereinafter referred to as angioplasty, is widely used in the treatment of occlusive vascular disease. However, it has been found that restenosis frequently occurs, and in the case of coronary angioplasty, restenosis occurs in about a third of cases within 6 months of the procedure.

Angiotensin converting enzyme (ACE) inhibitors or the physiologically tolerable salts thereof have been used in the treatment of atherosclerosis, thrombosis and/or peripheral vascular disease in mammals. It has been disclosed that, because ACE is predominantly localized in the luminal plasma membrane of the endothelial cell, ACE inhibitors can interfere in platelet-endothelium interaction. In addition, ACE inhibition potentiates the action of bradykinin (a strong stimulator of prostacyclin release from endothelial cells) by inhibiting its degradation. ACE inhibitors, consequently, have an inhibitory effect on platelet aggregation (See U.S. Pat. Nos. 5,140,012 and 5,166,143). In large scale clinical trials, ACE inhibitors have failed to demonstrate a beneficial effect in preventing restenosis following angioplasty.

Other methods for preventing restenosis after angioplasty include combining photoactivatable psoralen and ultraviolet radiation, as set forth in U.S. Pat. No. 5,116,864, and radiation from a source of radioactivity, as set forth in U.S. Pat. No. 5,213,561.

Recently, a gene has been discovered, that is present in certain families resident in Limone, Italy, which codes for a protein that may have the function of preventing the build-up of fatty deposits that clog the arteries and may be especially effective in preventing the reclogging of arteries that occurs after a blocked vessel has been cleared with balloon angioplasty surgery.

A commonly assigned, co-pending application, U.S. Ser. No. 08/794,289, describes methods of using RAR-selective retinoids and retinoid panagonists in treating restenosis.

A commonly assigned, co-pending application, U.S. Ser. No. 08/466,000, of Chandraratna, et al. describes 2,4-pentanedioic acid derivatives which have RXR-retinoid activity. Additionally, published PCT application 97/12853 discloses a variety of compounds which are dimer-selective RXR modulators.

Further, commonly assigned U.S. Pat. No. 5,455,265 and a divisional application pending therefrom describes and claims methods of treatment with certain compounds having selective agonist-like activity on RXR retinoid receptors.

Published PCT application 96/33724 discloses ligands that bind to and modulate the processes mediated by peroxisome proliferator activated receptor - gamma (PPARγ).

The above-mentioned patents and pending patent applications are incorporated herein by reference in their entirety. The portion of commonly assigned U.S. Pat. No. 5,455,265 to Chandraratna which details assays which are known and used in the art to measure RXR agonist activity and are described from column 5, line 37 through column 11, line 58 is specifically and expressly incorporated herein by reference.

To date, none of the present methods for preventing restenosis are suitable in every aspect. Therefore, the search for methods for preventing the onset of restenosis after angioplasty continues.

SUMMARY OF THE INVENTION

It has been discovered in accordance with the present invention that retinoid-like compounds which act selectively and preferably even specifically as agonists of the RXR receptor sites in preference to the RAR receptor sites, possess desirable therapeutic properties associated with retinoids, but without having one or more undesirable side effects of retinoids, such as teratogenicity or skin toxicity. For the purposes of the present invention, a compound is defined to be a specific or at least selective agonist of the RXR receptor site if the compound is at least approximately ten times more potent as an agonist at RXR receptor sites than at the RAR receptor sites.

Accordingly the present invention relates to methods of treating animals of the mammalian species, including humans, for preventing or reducing the occurrence of restenosis following any of the medically accepted angioplasty procedures with non-teratogenic compositions containing: 1) an RXR-specific agonist compound as defined above; 2) a combination of an RXR-specific agonist compound as defined above and a PPARγ-selective prostaglandin or prostaglandin-like compound including synthetic analogs such as the thiazolidinediones.

The present invention is also directed to the pharmaceutical compositions used in the above-noted methods of treatment.

DESCRIPTION OF THE DRAWINGS

In FIG. 6, bFGF induction was completely suppressed by 15-deoxy-$\Delta^{12,14}$-prostaglandin $J_2$ at a concentration of 1 µM even though bFGF induced DNA synthesis by almost three-fold. FIG. 7 demonstrates similar results for AGN 194204 used alone and FIG. 8 also shows similar inhibitions using AGN 192849, although it was not as active at 1 µM as AGN 194204.

In FIGS. 1–3 the abscissa of the chart expresses the percent absorption of light by the colored solution formed by incorporation as a percentage of a standard absorbance maximum. In FIGS. 3–8, the abscissa of the chart expresses the absolute absorbance of light at 450 nm. The calorimetric absorption varied proportionately with increasing incorporation of BrdU in replicated DNA.

DETAILED DESCRIPTION OF THE INVENTION

Figure 1:
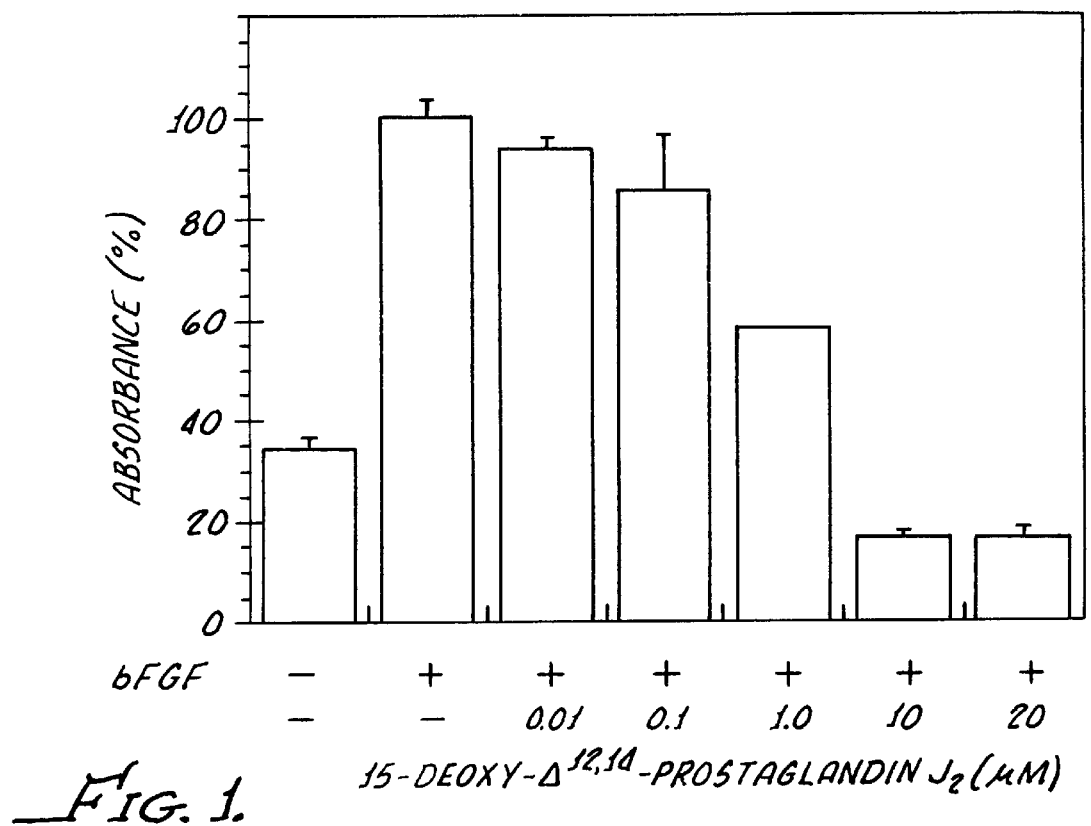
FIG. 1 is a bar graph showing data collected from our inhibition studies of rat aortic smooth muscle cell (R-AoSMC) proliferation by 15-deoxy-$\Delta^{12,14}$-prostaglandin $J_2$. It demonstrates that 15-deoxy-$\Delta^{12,14}$-prostaglandin $J_2$ inhibited the bFGF-induced proliferation of R-AoSMC to a level lower than that observed in quiescent uninduced cells (referring to first data point where bFGF was not present) at 10 and 20 $\mu$M concentrations. This inhibition of cell proliferation to less than that occurring in uninduced cells is regarded as complete inhibition. Note that significant inhibition of bFGF-induced cell proliferation was observed even at the 1 $\mu$M concentration of $PGJ_2$ analog The assay was a colorimetric measurement of cell proliferation as evidenced by the incorporation of BrdU in copies of the DNA.

Several factors which influence the vascular smooth muscle cell (VSMC) migration and proliferation have been identified by numerous researchers. These factors include, PDGF (platelet derived growth factor), IGF-I (insulin-like growth factor—I), IGF-II (insulin-like growth factor—II), aFGF, bFGF (fibroblast growth factors), thromboxane A2, serotonin, etc. Of these PDGF and bFGF have been shown to be important regulators of the VSMC chemoattraction and proliferation in the rat balloon-injury model resulting in arterial intimal hyperplasia which is used as an animal model of restenosis. PDGF is one of the most potent chemoattractants for VSMCs. The depletion of platelets and the administration of a PDGF neutralizing antibody results in inhibition of intimal thickening in balloon catheter injured rat arteries. Further, marked VSMC accumulation has been observed after exogenous administration of PDGF. bFGF, on the other hand, is a potent mitogen for VSMCs in vitro and in vivo. The administration of neutralizing bFGF antibodies inhibit VSMC proliferation in the injured rat carotid artery model. Further, by administration of bFGF neutralizing antibodies the PDGF-stimulated migration of the bovine smooth muscle cells in vitro is inhibited, thus indicating that the chemoattractant effects of the PDGF require bFGF.

These findings demonstrate that a proliferative stimulus may be required for PDGF to exert its chemoattractant action. Despite the demonstration that the blockade of the growth factor signal transduction pathways by the neutralizing antibodies or by antisense technology leads to the inhibition of post-injury intimal hyperplasia in the rat and restenosis in the pig, there are as yet no approved drugs for prevention of restenosis in humans based on these findings.

This decade has seen the introduction of synthetic peroxisome proliferator activated receptor gamma (PPARγ) analogs, the thiazolidinediones, as novel insulin-sensitizing agents that have demonstrated therapeutic efficacy in hyperglycemia and hyperinsulinemia in animal models of type II diabetes as well as in humans with non-insulin dependent diabetes mellitus. PPARγ is a ligand dependent transcription factor which belongs to the superfamily of steroid/thyroid/retinoid/vitamin $D_3$ nuclear receptors. A study has reported the inhibition of growth factor mediated proliferation of renal arteriolar smooth muscle cells by a thiazolidinedione analog, pioglitazone. See *Am. J. Physiol.*, 265 (4 Pt 2) pR726–32 (October 1993). Further, a recent thiazolidinedione analog, troglitazone, has been shown to inhibit the growth factor induced proliferation of rat arterial smooth muscle cells in vitro as well as VSMC intimal hyperplasia in vivo after endothelial injury in the rat.

It has been reported that PPARγ can heterodimerize with RXR-receptor ligands and function as a PPAR-RXR heterodimer in vitro and in vivo for the activation of PPAR-responsive genes. See Biochim. Biophys. Acta 1302 (2) pp93–109 (1996). Unexpectedly if has been discovered that an RXR ligand can perform PPARγ biological functions by acting through the RXR end of the heterodimer, alone. That is to say that an RXR specific agonist is capable of exerting the same effects as a PPARγ ligand when it binds to the RXR receptor of the PPARγ-RXR heterodimer. This is an unexpected result, since previously it was believed that only activated PPARγ receptors were capable of exerting a VSMC inhibiting effect. Thus, RXR compounds inhibit the growth factor induced proliferation of VSMCs in a manner analogous to the thiazolidinediones. As the accompanying figures demonstrate, an RXR-specific retinoid AGN 194204 completely inhibits the growth factor induced proliferation of rat aortic smooth muscle cells in vitro. It has also been found that AGN 194204 and another RXR-specific compound, AGN 192849, inhibit the bFGF induced proliferation of human aortic smooth muscle cells in vitro.

A further unexpected discovery of the present invention is that the combination of a PPARγ ligand and an RXR-specific retinoid give a synergistic effect in inhibition of VSMC proliferation. Our studies have demonstrated that AGN 194204 synergizes with a PPARγ ligand in inhibition of rat aortic smooth muscle cell proliferation. This finding is new since previously it was shown that activation of both receptors of the heterodimer affected transcription of target genes in an additive fashion. It was not known or expected that the combined activation would show synergistic effects, i.e. that the combined amount of the two receptor agonists required to inhibit VSMC proliferation would be less than the amount of one receptor agonist (to either the PPARγ ligand or the RXR ligand) alone.

In accordance with the present invention, a method is provided for preventing the onset, or reducing risk, of restenosis following angioplasty, wherein a therapeutically effective amount of an RXR specific retinoid is administered systemically, such as orally or parenterally, either alone or in conjunction with PPARγ-selective ligands. The retinoid, or combination of retinoid and prostaglandin, may be administered prior to, during and/or after the angioplasty procedure.

The term "restenosis" as employed herein is as defined by Serruys, P. W., et al, "Incidence of restenosis after successful coronary angioplasty; a time related phenomenon. A quantitative angiographic study in 342-consecutive patients at 1, 2, 3, and 4 months," Circulation 1988; 7:361–71.

In preferred embodiments where the patient to be treated in accordance with the present invention is normotensive, the retinoid can be administered without the side effects that can be experienced with administration of RAR specific retinoids such as teratogenicity and dermal and other side effects.

Further, when administered in conjunction with prostaglandin $J_2$ derivatives, the synergistic effect of the combination allows smaller doses of either compound to produce a therapeutic effect than can be achieved by the same dose of either agent alone. This combination further reduces the possibility of unwanted side effects.

The selective RXR agonists useful in the method of the present invention include compounds of the following formulae:

Formula I

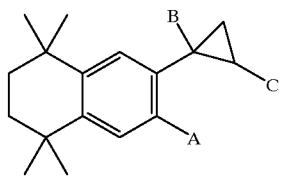

wherein B=methyl, A=hydrogen or methyl and C=

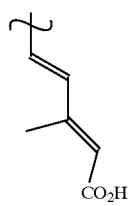

or wherein B=

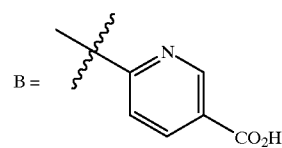

A=methyl, and C=hydrogen.

Formula II

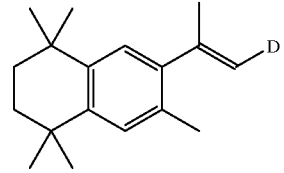

wherein D=

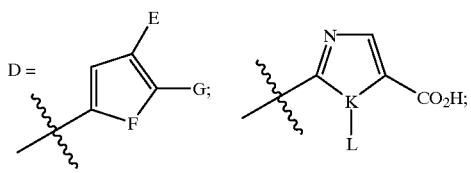

and wherein F is oxygen or sulfur and one of E and G is carboxy and the other is hydrogen; K is nitrogen or sulfur, when K is nitrogen L is hydrogen or —NSO$_2$NMe$_2$ and when K is sulfur L is absent.

Formula III

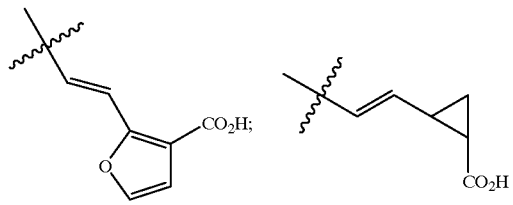

wherein M is nitrogen or carbon.

Preferred compounds of the invention are the compounds of formula II where the ring containing K is imidazole or where the ring containing F is thiophene and the compounds of formula III where M is carbon or nitrogen.

More preferred are the compounds of Formula II wherein the ring containing K is thiazole and of Formula III where the M is nitrogen or of formula I where C is pentadienoic acid.

Most preferred are the compounds of Formula I where B is nicotinic acid or C is pentadienoic acid as above, but further having the methyl substituent in the beta position and the pentadienoic acid in the alpha position, and the particularly preferred configuration occurs when the two asymmetric centers of the cyclopropyl ring both have the absolute stereochemical configuration of S.

Particularly preferred compounds of the present invention for use as PPARγ-selective ligands are: prostaglandin $J_2$ and its derivatives and prescursors, protaglandin-$D_2$ and its derivatives and prescursors, and the synthetic thiazolidinedione compounds, pioglitazone and troglitazone.

A pharmaceutically acceptable salt or ester or amide is any salt or ester or amide which retains the activity of the parent compound and does not impart any deleterious or undesirable effect on the subject to whom it is administered and in the context in which it is administered. It is contemplated that any of the carboxy groups of the compounds of the present invention can also be used advantageously as their salts or esters depending on the desired mode of administration. Such salts are those formed with pharmaceutically acceptable cations, e.g., alkali metals, alkali earth metals, amines, etc. Such esters and amides are those formed with pharmaceutically acceptable alcohols or amines such that when cleaved by enzymes the alcohol or amine molecule produced is non-toxic in the amounts released.

A geometric isomer is an isomer that differs from others of its family (i.e. those compounds which the same structure excepting the double bond geometry) by the geometry of the substituents at the double bond carbons contained in the compound. Typical designations for this isomerism are made by the nomenclature "E" (entgegen) and "Z" (zasummen). Although certain geometric isomers may be preferred in the practice of the present invention all are included within its scope.

The compounds referred to in the Figures and the Description of the Drawings have the following structures:

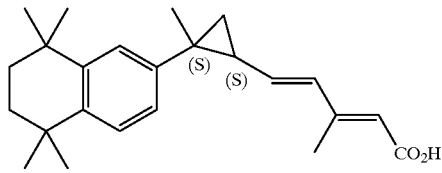

AGN 194204

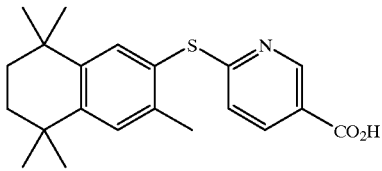

AGN 192849

(where each (S) indicates the absolute stereochemistry of the asymmetric center).

The compounds utilized in the method of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I through III or a corresponding pharmaceutically acceptable salt or ester thereof.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active compounds is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into units: doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 500 mg preferably 0.5 mg to 100 mg according to the particular application and the potency of the active component. The composition can, if desired, also contain other compatible therapeutic agents. In the case of a combination of drugs used to provide a therapeutic effect, the drugs can be formulated together in one composition or may be formulated separately into to different compositions which can be administered substantially simultaneously or at different times depending on the practitioner's design of the dosage regimen.

In therapeutic use, the compounds utilized in the method of this invention are administered at the initial dosage of about 0.01 mg to about 10 mg/kg daily. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The invention is further illustrated by the following non-limiting Examples.

EXAMPLE I

PPARγ Ligand and RXR Agonist Inhibition of bFGF-Induced Proliferation of VSMCs Rat aortic smooth muscle cells (R-AoSMC) were prepared from thoracic aorta of 3-month old Sprague-Dawly male rats by the explant technique. The cells were cultured in DMEM (Life Technologies, Gaithersberg, Md.) containing FBS (10%, Hyclone, Logan, Utah), antibiotic-antimycotic mixture (penicillin, 100 U/ml, streptomycin, 100 mg/ml, and amphotericin B, 250 ng/ml, Life Technologies, Gaithersberg, Md.) and L-glutamine (200 mM, Life Technologies, Gaithersberg, Md.). The purity and the identity of the smooth muscle cells was verified by immunostaining with a monoclonal antibody against smooth muscle α-actin (Sigma, St. Louis, Mo.). Immunostaining of rat aortic smooth muscle cellswas perfomred as follows: cells were plated 10,000 per chamber in an 8-chamber tissue culture slide (Nunc, Naperville, Ill.) overnight in DMEM containing FBS (10%). After 16 hours of incubation, cells were washed twice with phosphate buffered saline (PBS, Life Technologies, Gaithersberg, Md.), covered with methanol (−20° C.) and placed at −20° C. for 5 minutes. The cells were washed thrice with PBS and finally they were washed with PBS containing 1% bovine serum albumin (BSA, Sigma, St. Louis, Mo.). After draining the final wash solution, cells were incubated with monoclonal anti-α smooth muscle actin antibody (1:400 dilution in PBS containing 1% BSA) for 1 hour at 37° C. the slide was rinsed twice with PBS and the cells were incubated for 30 minutes at 37° C. with fluorescein conjugated goat anti-mouse IgG (Boehringer Mannheim, Indianapolis, Ind.) at a dilution of 1:40 with PBS containing 1% BSA. The cells were washed thrice with PBS, mounted with glycerol and visualized under UV light.

Human aortic smooth muscle cells (H-AoSMC) were obtained commercially (Clonetics, San Diego, Calif.). For cell proliferation experiments, 3–4 passaged rat or human aortic smooth muscle cells were grown to approx. 60% confluence and incubated overnight in 0.5% serum containing medium to achieve quiescent state. The quiescent cells were treated for 1 hour with bFGF and subsequently treated with $PGJ_2$ analog or RXR specific compounds for 24 hours. Cell proliferation was measured by incorporation of BrdU in the DNA and quantitated calorimetrically.

Figure 2:
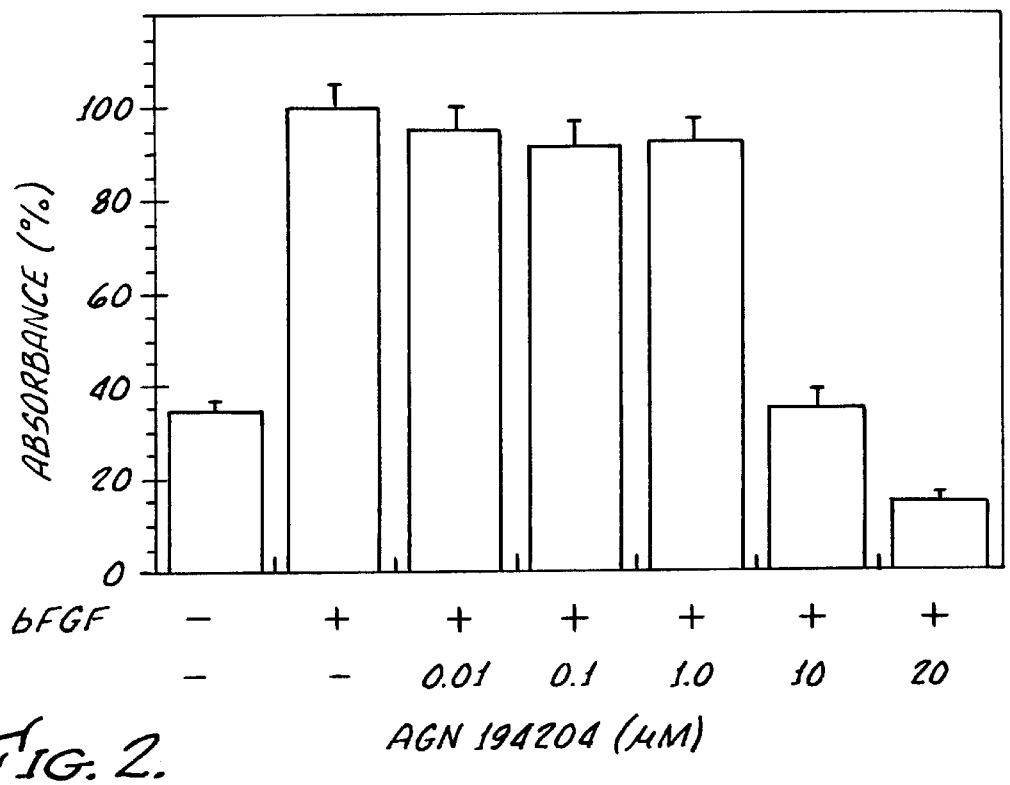
FIG. 2 is a bar graph showing data collected from our inhibition studies of rat aortic smooth muscle cell (R-AoSMC) proliferation by AGN 194204. It demonstrates that AGN 194204 inhibited the bFGF-induced proliferation of R-AoSMC to a level lower than that observed in quiescent uninduced cells (referring to first data point where bFGF was not present) at 20 µM and very slightly less than quiescent uninduced cells at 10 µM concentration. Here again, the assay was a colorimetric measurement of cell proliferation as evidenced by the incorporation of BrdU in copies of the DNA.
Figure 3:
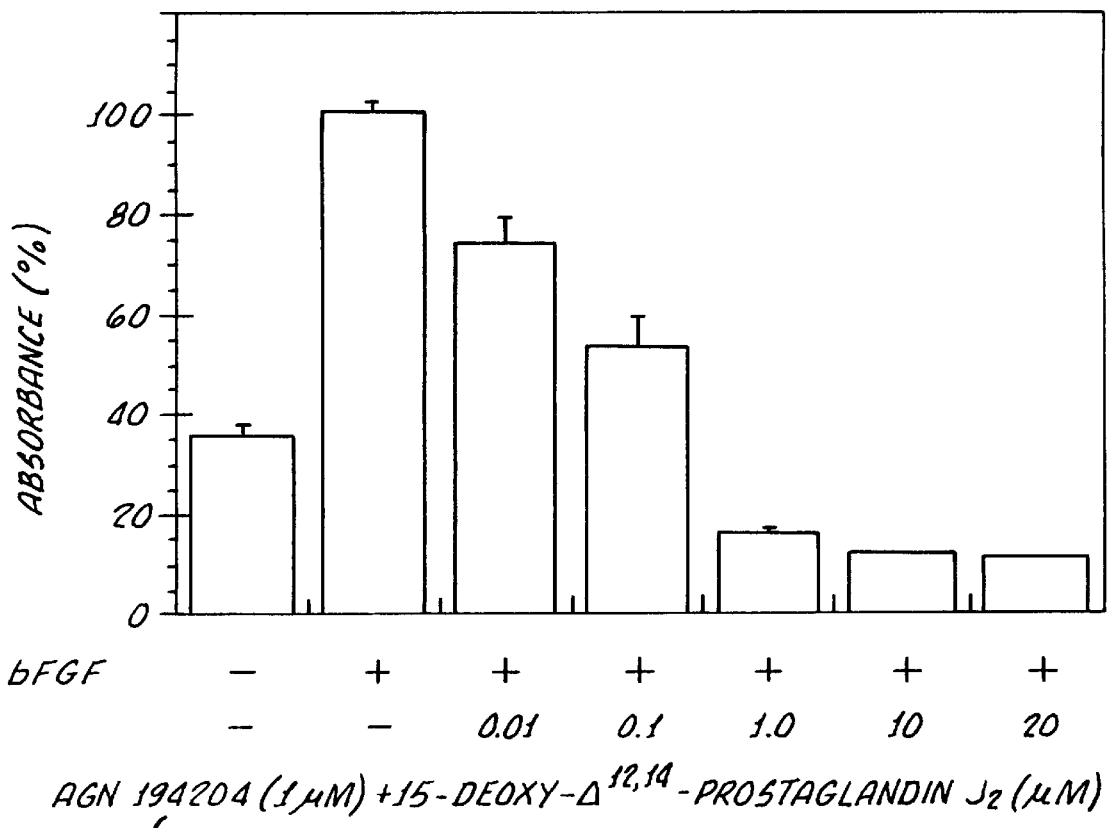
FIG. 3 is a bar graph showing data collected from inhibition studies using a steady concentration of AGN 194204 at 1 µM and variable concentrations of 15-deoxy-$\Delta^{12,14}$-prostaglandin $J_2$ in the presence of bFGF induction. The basal level of cell proliferation in the absence of bFGF is presented as the first bar in the figure. The study evidenced a synergism in the combination of the two compounds on the PPARγ-RXR heterodimer since 1 µM concentrations of each was sufficient to reduce the bFGF-induced proliferation of R-AoSMC to a level less than half of that observed in quiescent uninduced cells (referring to first data point where bFGF was not present). Here again, the assay was a colorimetric measurement of cell proliferation as evidenced by the incorporation of BrdU in copies of the DNA.

Measurement of BrdU incorporation and concomitantly DNA synthesis was made according to the following method. Incorporation of BrdU, the thymidine analog, into DNA was quantitated to determine the effect of PPARγ agonist (15-deoxy-$D^{12,14}$-$PGJ_2$, Cayman Chemical Co., Ann Arbor, Mich.) and RXR agonists on the growth factor (bFGF)-induced proliferation and DNA synthesis of R-AoSMCs and H-AoSMCs. For cell proliferation experiments, cells (3–4 passage) were plated at a density of 30,000 cells/well in 24 well plates (Costar, Cambridge, Mass.) in DMEM containing FBS (10%) for 24 hours. Thereafter cells were serum starved in DMEM-containing 0.05% FBS for 16 hours to achieve quiescent state. The quiescent cells were stimulated with the growth factor bFGF (20 ng/ml, Sigma, St. Louis, Mo.) for 1 hour and then treated with varying concentration of PPARγ agonist (15-deoxy-$D^{12,14}$-$PGJ_2$), RXR agonist (AGN 194204) or a combination of both agents for 24 hours in DMEM containing charcoal/dextrin-treated FBS (10%. Gemini Bioproducts Calabasas CA] The bromodeoxyuridine (brdU) incorporation assay was performed using a commercial kit that detects BrdU incorporation by ELISA (Boehringer Mannheim, Indianapolis, Ill.). BrdU incorporation was measured at 450 nm using a microplate ELISA reader (Molecular Devices, Sunnyvale, Calif.).

bFGF induced the proliferation rate of R-AoSMC by 3 folds (FIGS. 1–3). $PGJ_2$ analog (15-deoxy-$\Delta^{12,14}$-$PGJ_2$) completely inhibited the bFGF-induced proliferation of R-AoSMC to a level lower than that even observed in quiescent un-induced cells at 10 and 20 μM concentrations (FIG. 1). At 1.0 μM concentration, it inhibited the bFGF-induced growth of the aortic smooth muscle cells by approximately 50%. The RXR-specific ligand AGN 194204 also completely inhibited the proliferation of R-AoSMC at 10 and 20 μM concentrations (FIG. 2). However, it was slightly less potent than the $PGJ_2$ analog because it did not inhibit the proliferation of the aortic smooth muscle cells at 1.0 μM concentration.

EXAMPLE II

Synergy between PPARγ and RXR Agonists

Synergy between the two binding ligands of the PPARγ/RXR heterodimer was demonstrated using a $PGJ_2$ analog and AGN 194204. R-AoSMCs were treated with a fixed concentration of AGN 194204 (1.0 μM) and varying concentrations of agonist 15-deoxy-$\Delta^{12,14}$-$PGJ_2$ (0.01 to 20 μM). Note that AGN 194204 does not inhibit the growth of these cells at 1.0 μM concentration and the $PGJ_2$ analog does not show any significant inhibition at 0.1 μM concentration. In contrast, significant inhibition of the bFGF-induced growth of the R-AoSMCs was observed at 0.01 and 0.1 μM concentrations of the $PGJ_2$ analog along with 1.0 μM AGN 194204. One μM concentration of both the ligands completely inhibited the bFGF-induced growth of the R-AoSMCs. The results of this study demonstrate that RXR agonists and the PPARγ-specific ligands synergize in inhibitory activity to growth factor induced proliferation of the aortic smooth muscle cells since they provide complete inhibition at values 10 times less than the amount of either compound required to exert an equivalent effect alone.

EXAMPLE III

Inhibition of Aortic Smooth Muscle Cell Proliferation by AGN 192849

Figure 4:
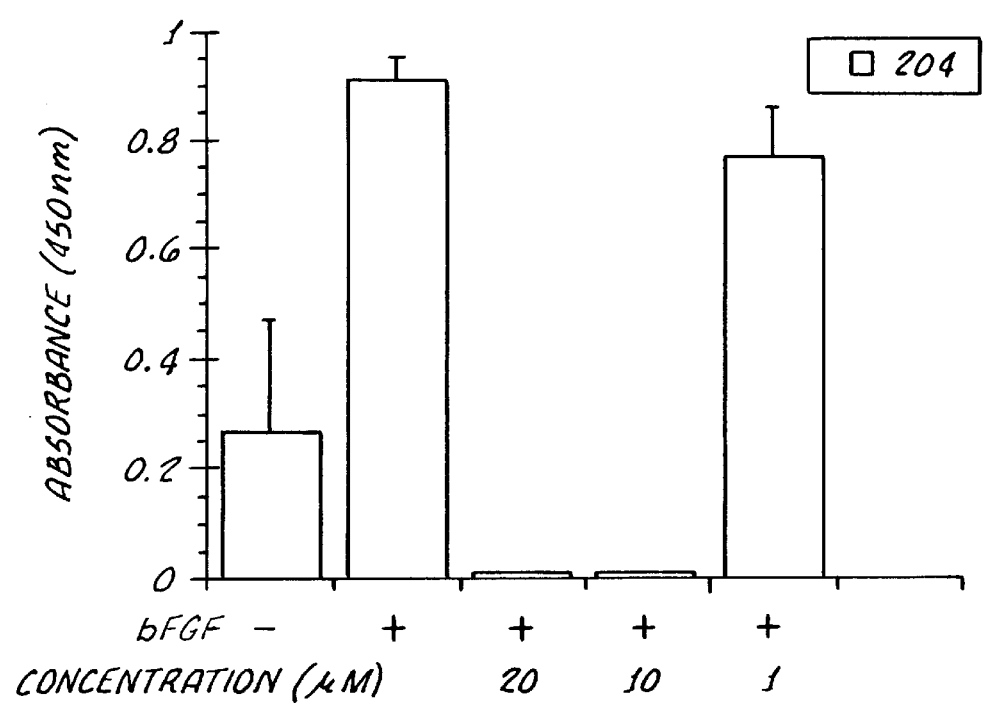
FIG. 4 and FIG. 5 are bar graphs that demonstrate our finding of very similar results in the inhibition of (R-AoSMC) proliferation by another RXR specific retinoid, AGN 192849 in comparison to AGN 194204 which was used in the studies summarized in FIGS. 1–3.
Figure 5:
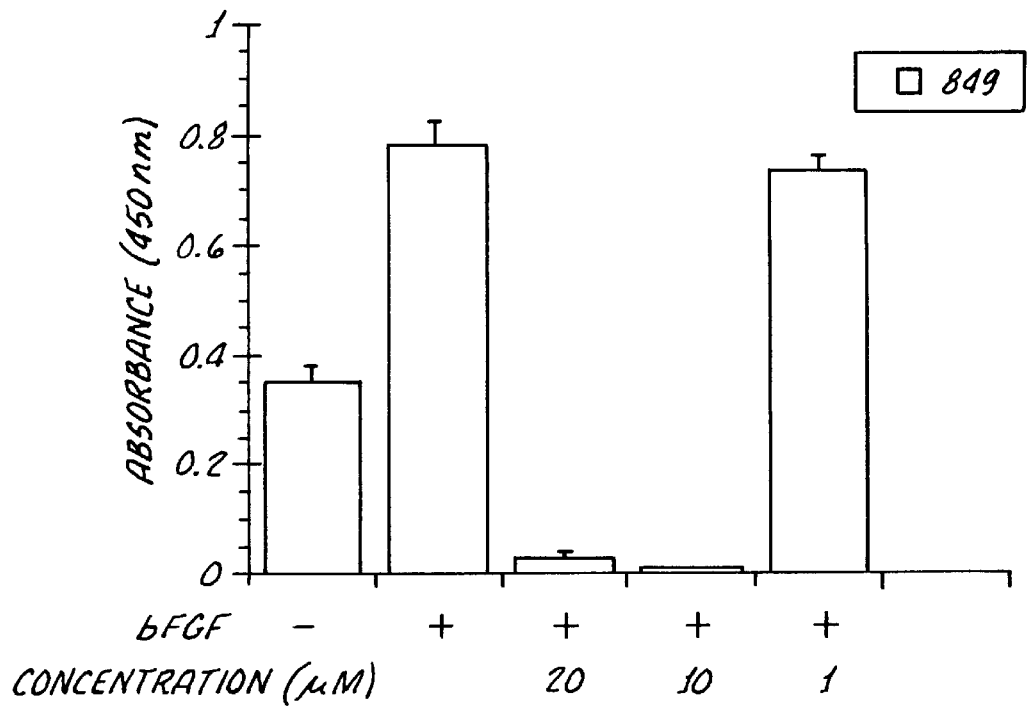

The ability of another RXR-specific retinoid, AGN 192849, in inhibition of the bFGF-induced proliferation of R-AoSMCs, was also tested. In this assay, bFGF induced the proliferation of the cells by 2 folds (FIGS. 4 and 5). Both AGN 194204 and AGN 192849 completely inhibited the proliferation of R-AoSMCs at 10 and 20 $\mu$M concentrations. Note that as observed earlier, the RXR-specific retinoids were not active at 1.0 $\mu$M concentration.

EXAMPLE IV

Figure 6:
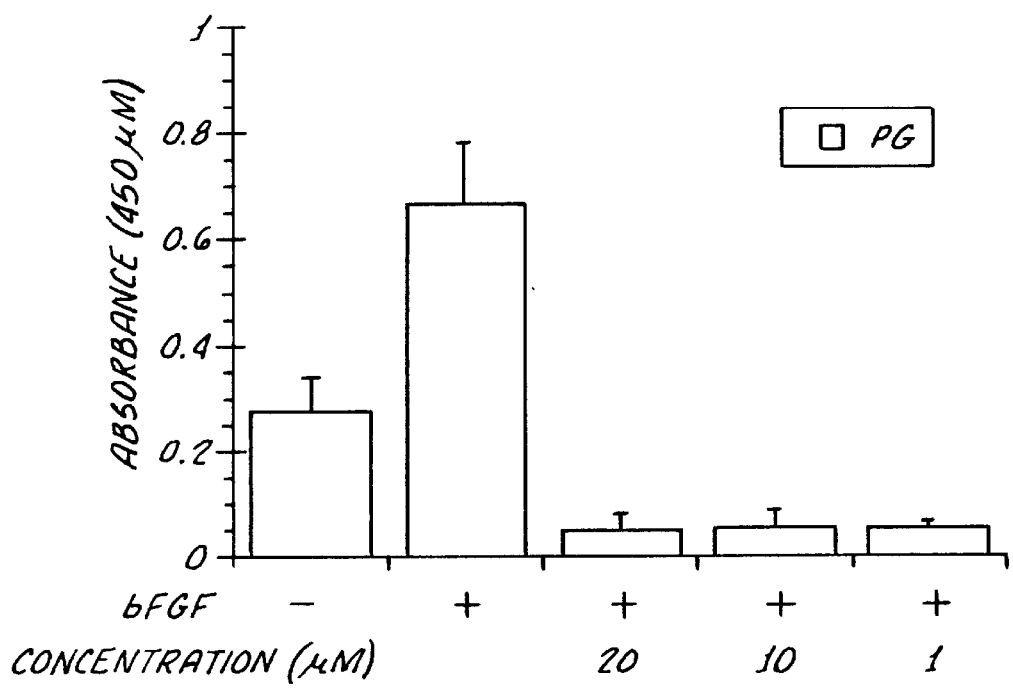
FIG. 6, FIG. 7 and FIG. 8 are bar graphs that illustrate both RXR and PPARγ-specific compounds also inhibit the proliferation of human aortic smooth muscle cells (H-AoSMC).
Figure 7:
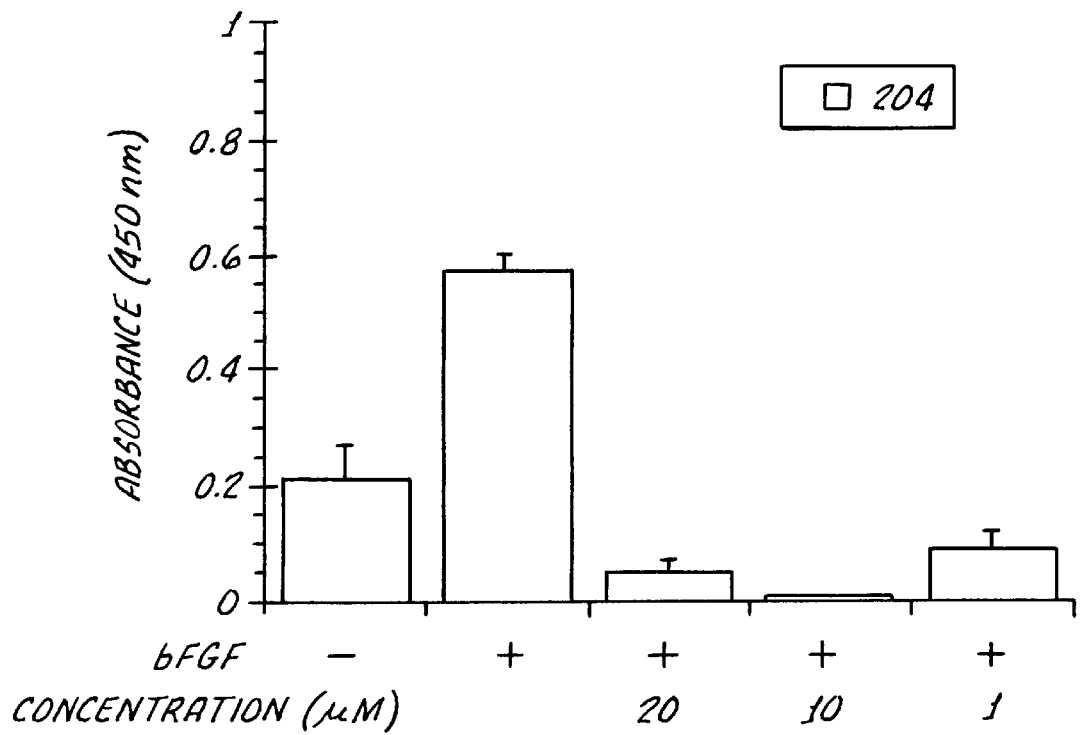
Figure 8:
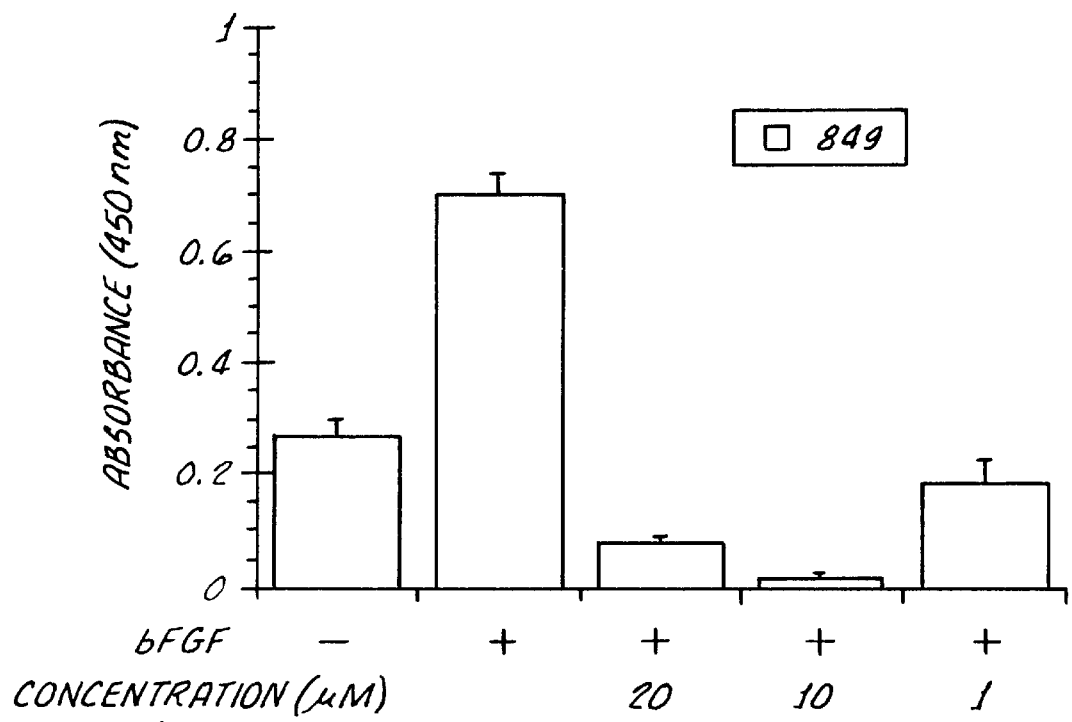

Inhibition of Growth Factor-Induced Proliferation of Human Aortic Smooth Muscle Cells (H-AoSMCs) by RXR and PPAR$\gamma$ Agonists To demonstrate that both RXR and PPAR$\gamma$-specific compounds also inhibit the proliferation of H-AoSMCs, the cells were treated with AGN 194204, AGN 192849 (RXR agonists) and the PPAR$\gamma$ agonist 15-deoxy-$\Delta^{12,14}$-PGJ$_2$. As shown in FIGS. 6–8, even 1 $\mu$M concentration of all three compounds was sufficient to completely inhibit the bFGF-induced proliferation of H-AoSMCs. Note that bFGF induced the DNA synthesis of these cells by 3-folds (FIGS. 6–8).

EXAMPLE V

AGN 194204 and PGJ$_2$ Analog are Not Cytotoxic for AoSMCs

Figure 9:
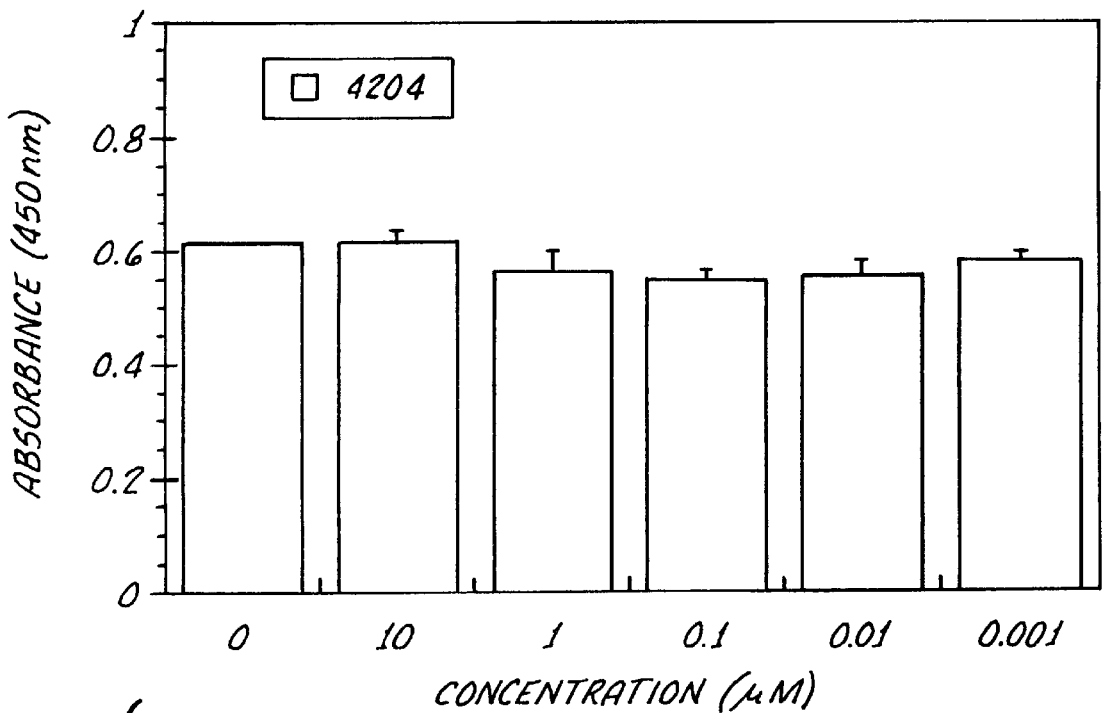
FIG. 9 and FIG. 10 are both bar graphs that demonstrate that AGN 194204 and 15-deoxy-$\Delta^{12,14}$-prostaglandin $J_2$, respectively, show no cytotoxicity to R-AoSMCs at concentrations up to 10 µM in comparison to an untreated control after 48 hr. Cell viability was assessed using a 3-[4,5-dimethylthiazol-2-yl]2,5diphenyltetrazolium bromide [MTT] assay that measures mitochondrial function, and again was based on colorimetric absorbance changes that vary proportionately with that function.
Figure 10:
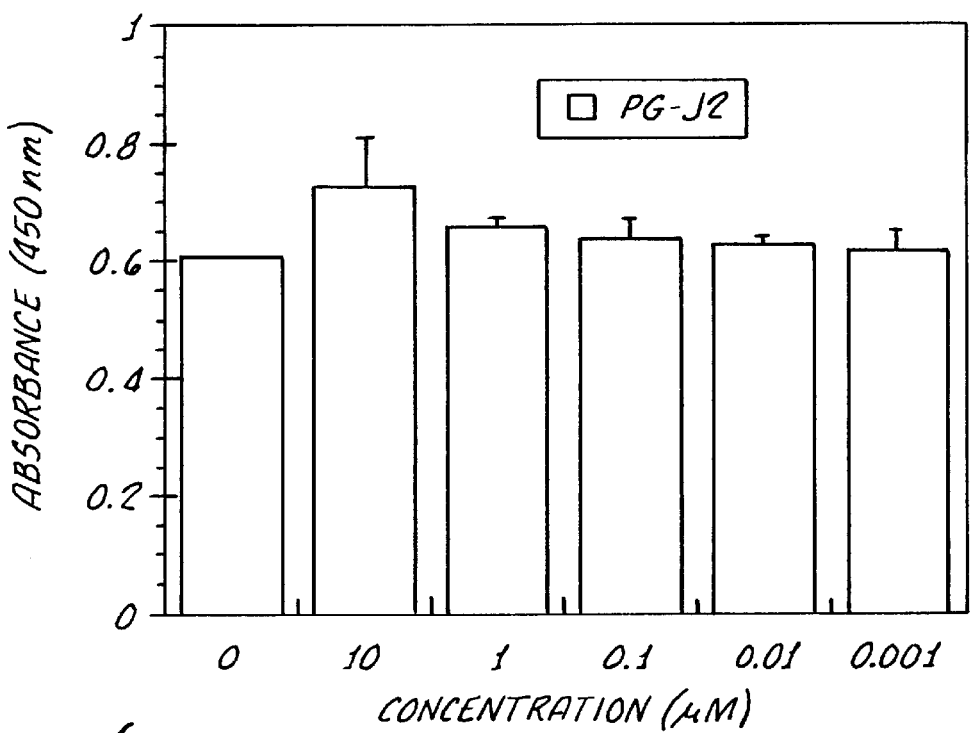

To confirm that the RXR and PPAR agonists are not cytotoxic for R-AoSMCs, cell viability was assessed using 3-[4,5-dimethylthiazol-2-yl]-2,5-diphenyltetrazolium bromide assay (MTT) that measures mitochondrial function. The data in FIGS. 9 and 10 show that AGN 194204 and 15-deoxy-$\Delta^{12,14}$-PGJ$_2$ had no effect even up to 10 $\mu$M concentration on cell viability as indicated by equivalent mitochondrial activity in control and AGN 194204/15-deoxy-$\Delta^{12,14}$-PGJ$_2$-treated R-AoSMCs after 48 hours. The MTT assay for cell viability was conducted according to the following protocol. A colorimetric assay based on the ability of living cells to reduce the yellow salt MTT (3-[4,5-dimethylthiozol-2-yl]-2,5 diphenyl tetrazolium bromide) to formazan was used to measure cell viability. Cells were treated for 48 hours with 0.001 to 10 $\mu$M PPAR$\gamma$ agonist (15-deoxy-D$^{12,14}$-PGJ$_2$) or the RXR agonist (AGN 194204). Cell viability was measured by the MTT assay kit as per the manufacturer's instructions (Promega, Madison, Wis.). The formation of formazan was quantitated by measuring absorbance at 570 nm using a microplate ELISA reader (Molecular Devices, Sunnyvale, Calif.).

While particular embodiments of the invention have been described, it will be understood that the invention is not, of course, limited thereto since many obvious modifications can be made, and it is intended to include within this invention any such modification as will fall within the scope of the appended claims.

Having now described the invention, we claim:

1. A method for preventing or reducing the occurrence of restenosis following angioplasty which comprises administering to a mammal in need of such treatment synergistic effective amounts of an RXR-specific retinoid in conjunction with, at substantially the same or different times, a PPAR$\gamma$-selective ligand and pharmaceutically acceptable salts, esters, and amides of either or both.

2. The method of claim 1 wherein the effective amounts of the RXR-specific retinoid and PPAR$\gamma$-selective ligand are administered together in the same dosage formulation.

3. The method of claim 1 wherein the effective amounts of the RXR-specific retinoid and PPAR$\gamma$-selective ligand are administered separately in different dosage formulations.

4. The method of claim 1 wherein the retinoid is selected from the group of compounds consisting of Formula III

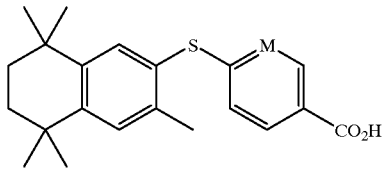

Formula III wherein M is nitrogen or carbon.

5. The method of claim 1 wherein the retinoid is selected from the group of compounds consisting of Formula II

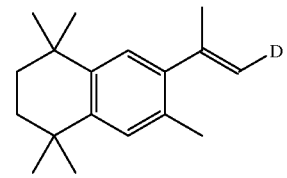

Formula II wherein D=

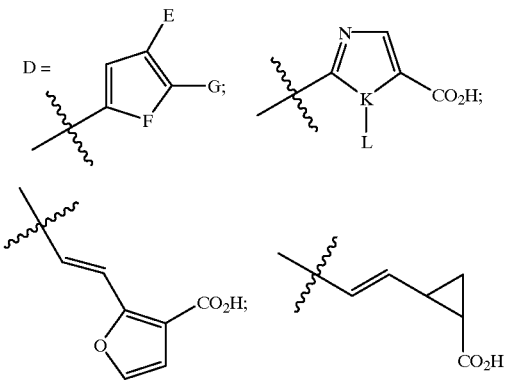

and wherein F is oxygen or sulfur and one of E and G is carboxy and the other is hydrogen; K is nitrogen or sulfur and when K is nitrogen L is hydrogen or —NSO$_2$NMe$_2$ and when K is sulfur L is absent.

6. The method of claim 1 wherein the retinoid is selected from the group of compounds consisting of Formula I

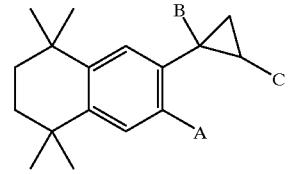

Formula I wherein B=methyl, A=hydrogen or methyl and C=

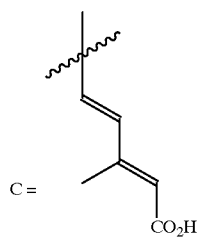

C = or wherein B=

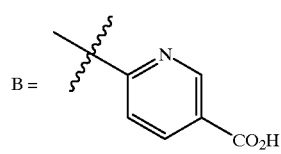

A=methyl, and C=hydrogen.

7. The method of claim 1 wherein the PPARγ-selective ligand is selected from the group of compounds consisting of prostaglandin-J2 and its derivatives and precursors, protaglandin-D2 and its derivatives and precursors, and the thiazolidinedione compounds, pioglitazone and troglitazone.

8. The method of claim 1 wherein said retinoid and said PPARγ-selective ligand are administered in a single dose or divided doses of from about 0.1 to about 200 mg, one to four times daily.

9. The method of claim 1 wherein said combination of retinoid and PPARγ ligand is administered during angioplasty.

10. The method of claim 1 wherein said combination of retinoid and PPARγ ligand is administered before angioplasty.

11. The method of claim 1 wherein said combination of retinoid and PPARγ ligand is administered after angioplasty.

12. The method of claim 1 wherein the retinoid is

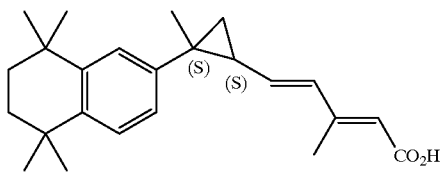

and the PPARγ ligand is 15-deoxy-$\Delta^{12,14}$-PGJ$_2$.

13. A pharmaceutical composition in a dosage form suitable for use in preventing or reducing the risk of restenosis following angioplasty which comprises synergistic effective amounts of an RXR-specific retinoid, a PPARγ-selective ligand and a pharmaceutically acceptable carrier.

14. The composition of claim 13 wherein said dosage form is in injectable or other parenteral form.

15. The composition of claim 13 wherein said dosage form is an oral dosage form.

16. The composition of claim 13 wherein the retinoid is selected from the group of compounds consisting of Formula III

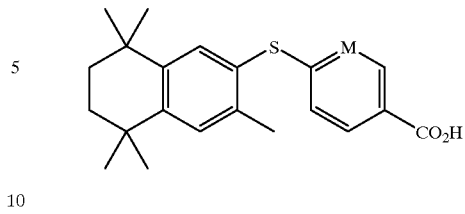

Formula III wherein M is nitrogen or carbon.

17. The composition of claim 13 wherein the retinoid is selected from the group of compounds consisting of Formula II

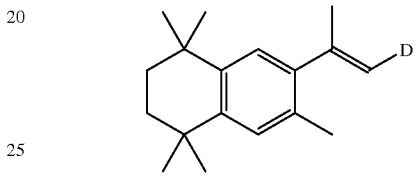

Formula II wherein D=

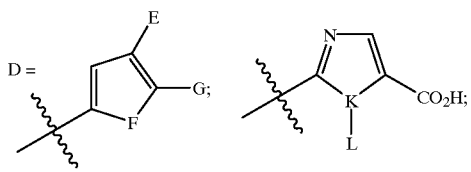

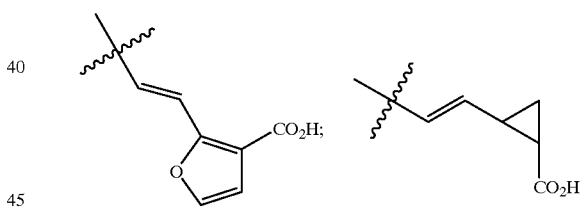

and wherein F is oxygen or sulfur and one of E and G is carboxy and the other is hydrogen; K is nitrogen or sulfur and when K is nitrogen L is hydrogen or —NSO$_2$NMe$_2$ and when K is sulfur L is absent.

18. The composition of claim 13 wherein the retinoid is selected from the group of compounds consisting of Formula I

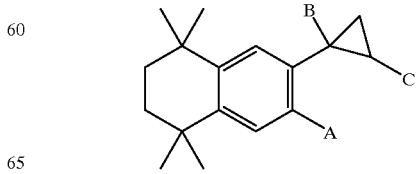

Formula I wherein B=methyl, A=hydrogen or methyl and C=

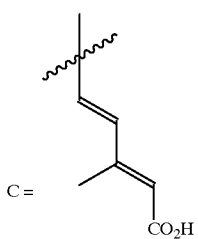

or wherein B=

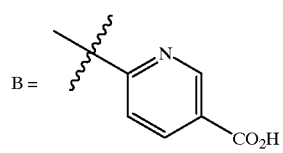

A=methyl, and C=hydrogen.

19. The composition of claim 13 wherein the PPARγ-selective ligand is selected from the group of compounds consisting of prostaglandin-J2 and its derivatives and precursors, protaglandin-D2 and its derivatives and precursors, and the thiazolidinedione compounds, pioglitazone and troglitazone.

20. The composition of claim 18 wherein the retinoid is

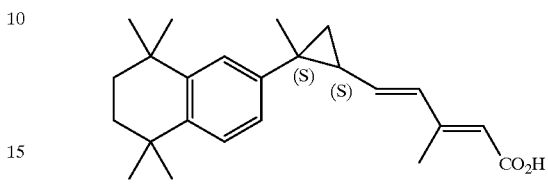

and the PPARγ ligand is 15-deoxy-$\Delta^{12,14}$-PGJ$_2$.

* * * * *

UNITED STATES PATENT AND TRADEMARK OFFICE
CERTIFICATE OF CORRECTION

PATENT NO. : 6,034,110
DATED : March 7, 2000
INVENTOR(S) : Nagpal et al

It is certified that error appears in the above-indentified patent and that said Letters Patent is hereby corrected as shown below:

Column 2, line 62; after "analog" insert --.--
Column 3, line 51; after second occurrence of "5" insert -- - --
Column 9, line 37; delete "cellswas" and insert in place thereof --cells were--
Column 9, line 37; delete "perfomred" and insert in place thereof --performed--
Column 9, line 65; delete "calorimetrically" and insert in place thereof --colorimetrically--
Column 16, line 4, claim 19; delete "protaglandin" and insert in place thereof --prostaglandin--

Signed and Sealed this

Thirteenth Day of February, 2001

Attest:

NICHOLAS P. GODICI

Attesting Officer

Acting Director of the United States Patent and Trademark Office